United States Patent [19]
Bandman et al.

[11] Patent Number: 6,156,523
[45] Date of Patent: Dec. 5, 2000

[54] SERINE/THREONINE PROTEIN KINASES

[75] Inventors: Olga Bandman, Mountain View; Y. Tom Tang; Surya K. Goli, both of San Jose; Neil C. Corley, Mountain View; Karl J. Guegler, Menlo Park; Gina A. Gorgone, Boulder Creek; Jennifer L. Hillman, Mountain View, all of Calif.

[73] Assignee: Incyte Pharmaceuticals, Inc., Palo Alto, Calif.

[21] Appl. No.: 09/153,939

[22] Filed: Sep. 16, 1998

Related U.S. Application Data

[63] Continuation-in-part of application No. 08/749,902, Nov. 15, 1996, Pat. No. 5,985,635.

[51] Int. Cl.[7] .......................... A61K 38/43; C12N 15/52; C12N 9/00; C07K 14/00; G01N 23/53
[52] U.S. Cl. .......................... 435/7.1; 424/94.1; 424/94.3; 435/69.1; 435/183; 435/194; 530/350; 536/23.1; 536/23.5
[58] Field of Search ................................. 424/94.1, 94.3; 435/69.1, 183, 194; 530/350; 536/23.1, 23.5

[56] References Cited

PUBLICATIONS

Harmann, B. and Kilimann, MW. cDNA encoding a 59 kDa homolog of ribosomal protein S6 kinase from rabbit iver. 1990 FEBSLetters. vol. 273 No. 1,2, pp. 248–252.

Waskiewicz A.J., et al., (Direct Submission), GenBank Sequence Database (Accession Y11092), National Center for Biotechnology Information, National Library of Medicine, Bethesda, Maryland, 20894 (GI 192906).

Kilimann, M.W., et al., (Direct Submission), GenBank Sequence Database (Accession X54415), National Center for Biotechnology Information, National Library of Medicine, Bethesda, Maryland, 20894 (GI 1562).

*Primary Examiner*—Prema Mertz
*Assistant Examiner*—Joseph F. Murphy
*Attorney, Agent, or Firm*—Incyte Pharmaceuticals, Inc.; Lynn E. Murry

[57] ABSTRACT

The invention provides human serine/threonine protein kinases (HSTK) and polynucleotides which identify and encode HSTK. The invention also provides expression vectors, host cells, antibodies, agonists, and antagonists. The invention also provides methods for diagnosing, treating or preventing disorders associated with expression of HSTK.

5 Claims, 14 Drawing Sheets

```
      10           19           28           37           46           55
5' G TAT CNC TGC CAN GGN GGC CCC CAC CCN AAA NCA GGG GGG TNG GGG CCG GCC GGC 64           73           82           91          100          109
CAG GGC CAT GTC CTG AGN CCC CNN GGC GTG CCT CCT GGA ACA GAT ATG CCC GCC
                                                              M   P   A 118          127          136          145          154          163
AGC CAG CCC ATT GAC NTC CCG GGC GCC AAG AAN AGG GGC AAG AAN AAT AAG CGC
 S   Q   P   I   D   X   P   G   A   K   X   R   G   K   X   N   K   R 172          181          190          199          208          217
GGC CGG ACC GAC AGC TTC TCG GGC GCT CAT GCC CGA AGG TTT GAA NAC GTC TAC CAN CTG CAG
 G   R   T   D   S   F   S   G   A   H   A   R   R   F   E   X   V   Y   X   L   Q 226          235          244          253          262          271
GAA NAT NTG CTG GGG GAG GGC GCT CAT GCC CGA GTG CAG ACC TGC ATT AAC CTG
 E   X   X   L   G   E   G   A   H   A   R   V   Q   T   C   I   N   L 280          289          298          307          316          325
ATC ACC AGC CAG GAG TAC NCC GTC AAN ATC ATT GNT TTT TTT NCA GGC CAC ATT
 I   T   S   Q   E   Y   X   V   X   I   I   X   F   F   X   G   H   I 334          343          352          361          370          379
CGG AGC AGG GTT TTC AGG GAG GTG GAG ATG CTG TAC CAG TGC CAG GGA CAC AGG
 R   S   R   V   F   R   E   V   E   M   L   Y   Q   C   Q   G   H   R
```

FIGURE 1A

```
      388             397       406       415       424       433
AAC GTC CTA GAG CTA ATT GAG TTC TTC GAG GAG GAC CGC TTC TAC CTG GTG
 N   V   L   E   L   I   E   F   F   E   E   D   R   F   Y   L   V 442             451       460       469       478       487
TTT GAG AAG ATG CGG GGA GGC TCC ATC CTG AGC CAC ATC AAG CGC CGG CAC
 F   E   K   M   R   G   G   S   I   L   S   H   I   K   R   R   H 496             505       514       523       532       541
TTC AAC GAG CTG GAG GCC AGC GTG GTG CAG GAC GTG GCC AGC GCC TTG GAC
 F   N   E   L   E   A   S   V   V   Q   D   V   A   S   A   L   D 550             559       568       577       586       595
TTT CTG CAT AAC AAA GGC ATC GCC CAC AGG GAC CTA AAG CCG GAA AAC ATC CTC
 F   L   H   N   K   G   I   A   H   R   D   L   K   P   E   N   I   L 604             613       622       631       640       649
TGT GAG CAC CCC AAC CAG GTC TCC CCC GTG AAG ATC TGT GAC TTC GAC CTG GGC
 C   E   H   P   N   Q   V   S   P   V   K   I   C   D   F   D   L   G 658             667       676       685       694       703
AGC GGC ATC AAA CTC AAC GGG GAC TGC TCC CCT ATC TCC ACC CCG GAG CTG CTC
 S   G   I   K   L   N   G   D   C   S   P   I   S   T   P   E   L   L 712             721       730       739       748       757
ACT CCG TGC GGC TCG GCG GAG TAC ATG GCC CCG GAG GTA GTG GAG GCC TTC AGC
 T   P   C   G   S   A   E   Y   M   A   P   E   V   V   E   A   F   S
```

FIGURE 1B

```
                                       766         775         784         793         802         811
                                   GAG GAG GCT AGC ATC TAC GAC AAG CGC TGC GAC CTG TGG AGC CTG GGC GTC ATC
                                    E   E   A   S   I   Y   D   K   R   C   D   L   W   S   L   G   V   I 820         829         838         847         856         865
                                   TTG TAT ATC CTA CTC AGC GGC TAC CCG CCC TTC GTG GGC CGC TGG TGG CAG CGA
                                    L   Y   I   L   L   S   G   Y   P   P   F   V   G   R   W   W   Q   R 874         883         892         901         910         919
                                   CTG CGG CTG GGA CCG ATG TAC GAC ATG CTC ACT GGA TCG CCG CCC TTT ACC
                                    L   R   L   G   P   M   Y   D   M   L   T   G   S   P   P   F   T 928         937         946         955         964         973
                                   GCA GAG AAC CGG AAG AAA ACC ATG GAT AAG ATC AGG GGC AAG CTG GCA CTN
                                    A   E   N   R   K   K   T   M   D   K   I   R   G   K   L   A   L 982         991        1000        1009        1018        1027
                                   CCC CCC TAC CTC ACC CCA GAT GCC CGG GAC CTT GTC AAA AAG TTT CTG AAA CGG
                                    P   P   Y   L   T   P   D   A   R   D   L   V   K   K   F   L   K   R 1036        1045        1054        1063        1072        1081
                                   AAT CCC AGC CAG CGG ATT GGG GGT GGC CCA GGG GAT GCT GCT GAT GTG CAG AGA
                                    N   P   S   Q   R   I   G   G   G   P   G   D   A   A   D   V   Q   R 1090        1099        1108        1117        1126        1135
                                   CAT CCC TTT TTC CGG CAC ATG AAT TGG GAC GAC CTT CTG GCC TGG CGT GTG GAC
                                    H   P   F   F   R   H   M   N   W   D   D   L   L   A   W   R   V   D
```

FIGURE 1C

```
      1144           1153           1162           1171           1180           1189
CCC CCT TTC AGG CCC TGT CTG CAG TCA GAG GAG GAC GTG AGC CAG TTT GAT ACC
 P   P   F   R   P   C   L   Q   S   E   E   D   V   S   Q   F   D   T 1198           1207           1216           1225           1234           1243
CGC TTC ACA CGG CAG ACG CCG GTG ACG GAC AGT CCT GAT GAC ACA GCC CTC AGC GAG
 R   F   T   R   Q   T   P   V   T   D   S   P   D   D   T   A   L   S   E 1252           1261           1270           1279           1288           1297
AGT GCC AAC CAG GCC TTC CTG GGC TTC ACA TAC GTG GCG CCG TCT GTC CTG GAC
 S   A   N   Q   A   F   L   G   F   T   Y   V   A   P   S   V   L   D 1306           1315           1324           1333           1342           1351
AGC ATC AAG GAG GGC TTC TCC TTC CAG CCC AAG CTG CGC TCA CCC AGG CGC CTC
 S   I   K   E   G   F   S   F   Q   P   K   L   R   S   P   R   R   L 1360           1369           1378           1387           1396           1405
AAC AGT AGC CCC CGG GTC CCC GTC AGC CTG CCC ACG GAG CCC ACG GAG TTC TCC CCT TTT GAG GGG
 N   S   S   P   R   V   P   V   S   L   P   T   E   P   T   E   F   S   P   F   E   G 1414           1423           1432           1441           1450           1459
TTT CGG CCC AGC CCC AGC CTG CCG GAG CCC ACG GAG CTA CCT CTA CCT CCA CTC
 F   R   P   S   P   S   L   P   E   P   T   E   L   P   L   P   P   L 1468           1477           1486           1495           1504           1513
CTG CCA CCG CCG CCG TCG ACC ACC GCC CCT CTC CCC ATC CGT CCC CCC TCA
 L   P   P   P   P   S   T   T   A   P   L   P   I   R   P   P   S
```

FIGURE 1D

```
      1522           1531           1540           1549           1558           1567
GGG ACC AAG AAG TCC AAG AGG GGC CGT GGG CGT CCA GGG CGT AGG AAG CCG GGT
 G   T   K   K   S   K   R   G   R   G   R   P   G   R   R   K   P   G 1576           1585           1594           1603
GGG GGT GAG GGT AGC CCT TGA GCC CTG TCC CTG CGG CTG T 3'
 G   G   E   G   S   P   *
```

FIGURE 1E

```
                    10           19           28           37           46           55
5'C GAC GGG CCC GCG GCG CGC CAT GGC GCN NGT GTT TGA TTT GGA TTT GGA GAC
       64           73           82           91          100          109
GGA GGA AGG CAG CGA GGG CGA GGG CGA GCC AGA GCT CAG CCC CGC GGC CTG TGG
      118          127          136          145          154          163
GAC ACT ATG AAG AGG TGG AGC TGA CTG AGA GCG TGA ACG TTG GCC CAG AGC
      172          181          190          199          208          217
GCA TCG GGC CCC ACT GCT TTG AGC TGC TGC GTG TGC TGG GCA AGG GGG GCT ATG
      226          235          244          253          262          271
GCA AGG TGT TCC AGG TGC GAA AGG TGC AAG GCA CCA ACT TGG GCA AAA TAT ATG
      280          289          298          307          316          325
CCA TGA AAG TCC TAA GGA AGG CCA AAA TTG TGC GCA ATG CCA AGG ACA CAG CAC
      334          343          352          361          370          379
ACA CAC GGG CTG AGC GGA ACA TTC TAG AGT CAG TGA AGC ACC CCT TTA TTG TGG
      388          397          406          415          424          433
AAC TGG CCT ATG CCT TCC AGA CTG GTG GCA AAC TCT ACC TCG TCC TTG AGT GCC
    M   P   M   P   S   R   L   V   A   N   S   T   S   S   L   S   A

FIGURE 2A
```

```
                                      442              451              460              469              478              487
                                      TCA GTG GCG AGC TCT TCC TGG GAA GAT ACG GCC TTC TAC CTG GCT GAG
                                      S   V   A   S   S   S   W   E   D   T   A   C   F   Y   L   A   E 496              505              514              523              532              541
                                      ATC ACG CTG GCC CTG GGC CAT CTC CAC TCC CAG GGC TGC TAC CGG GAC CTC
                                      I   T   L   A   L   G   H   L   H   S   Q   G   I   Y   R   D   L 550              559              568              577              586              595
                                      AAG CCC GAG AAC ATC ATG CTC AGC AGC CAG GGC CAC ATC AAA CTG ACC GAC TTT
                                      K   P   E   N   I   M   L   S   S   Q   G   H   I   K   L   T   D   F 604              613              622              631              640              649
                                      GGA CTC TGC AAG GAG TCA ATC CAT GAG GGC GCC GTC ACT CAC AAC TTC TGC GGC
                                      G   L   C   K   E   S   I   H   E   G   A   V   T   H   N   F   C   G 658              667              676              685              694              703
                                      ACC ATT GAG TAC ATG GCC CCT GAG ATT CTG GTG CGC AGT GGC CAC AAC CGG GCT
                                      T   I   E   Y   M   A   P   E   I   L   V   R   S   G   H   N   R   A 712              721              730              739              748              757
                                      GTG GAC TGG TGG AGC CTG GGG GCC CTG ATG TAC GAC ATG CTC ACT GGA TCG CCG
                                      V   D   W   W   S   L   G   A   L   M   Y   D   M   L   T   G   S   P 766              775              784              793              802              811
                                      CCC TTT ACC GCA GAG AAC CGG AAG AAA ACC ATG GAT AAG ATC ATC AGG GGC AAG
                                      P   F   T   A   E   N   R   K   K   T   M   D   K   I   I   R   G   K
```

FIGURE 2B

| | | 820 | | 829 | | 838 | | 847 | | 856 | | 865 |
|---|---|---|---|---|---|---|---|---|---|---|---|---|
| CTG | GCA | CTG | CCC | CCC | TAC | CTC | ACC | CCA | GAT | GCC | CGG | GAC | CTT | GTC | AAA | AAG | TTT |
| L | A | L | P | P | Y | L | T | P | D | A | R | D | L | V | K | K | F |

| | | 874 | | 883 | | 892 | | 901 | | 910 | | 919 |
|---|---|---|---|---|---|---|---|---|---|---|---|---|
| CTG | AAA | AAT | CCC | AGC | CAG | CGG | ATT | GGG | GGT | CCA | GGG | GAT | GCT | GCT | GAT |
| L | K | N | P | S | Q | R | I | G | G | P | G | D | A | A | D |

| | | 928 | | 937 | | 946 | | 955 | | 964 | | 973 |
|---|---|---|---|---|---|---|---|---|---|---|---|---|
| GTG | CAG | AGA | CAT | CCC | TTT | TTC | CGG | CAC | ATG | AAT | TGG | GAC | GAC | CTT | CTG | GCC | TGG |
| V | Q | R | H | P | F | F | R | H | M | N | W | D | D | L | L | A | W |

| | | 982 | | 991 | | 1000 | | 1009 | | 1018 | | 1027 |
|---|---|---|---|---|---|---|---|---|---|---|---|---|
| CGT | GTG | GAC | CCC | CCT | TTC | AGG | CCC | CTG | TGT | CTG | CAG | GCC | GTG | GAC | GAG | GTG | AGC | CAG |
| R | V | D | P | P | F | R | P | L | C | L | Q | A | V | D | E | V | S | Q |

| | | 1036 | | 1045 | | 1054 | | 1063 | | 1072 | | 1081 |
|---|---|---|---|---|---|---|---|---|---|---|---|---|
| TTT | GAT | ACC | CGC | TTC | ACA | CGG | CAG | ACG | CCG | GTG | GAC | AGT | CCT | GAT | GAC | ACA | GCC |
| F | D | T | R | F | T | R | Q | T | P | V | D | S | P | D | D | T | A |

| | | 1090 | | 1099 | | 1108 | | 1117 | | 1126 | | 1135 |
|---|---|---|---|---|---|---|---|---|---|---|---|---|
| CTC | AGC | GAG | AGT | GCC | AAC | CAG | GCC | TTC | CTG | GGC | TTC | ACA | TAC | GTG | GCG | CCG | TCT |
| L | S | E | S | A | N | Q | A | F | L | G | F | T | Y | V | A | P | S |

| | | 1144 | | 1153 | | 1162 | | 1171 | | 1180 | | 1189 |
|---|---|---|---|---|---|---|---|---|---|---|---|---|
| GTC | CTG | GAC | AGC | ATC | AAG | GAG | GGC | TTC | TCC | TTC | CAG | CCC | AAG | CTG | CGC | TCA | CCC |
| V | L | D | S | I | K | E | G | F | S | F | Q | P | K | L | R | S | P |

FIGURE 2C

```
                                      1198      1207      1216      1225      1234      1243
                                 AGG CGC CTC AAC AGT AGC CCC CGG GTC CCC AGC CCC CTC AAG TTC TCC CCT
                                  R   R   L   N   S   S   P   R   V   P   S   P   L   K   F   S   P 1252      1261      1270      1279      1288      1297
                                 TTT GAG GGG TTT CGG CCC AGC CCC AGC CTG CCG GAG CCC ACG GAG CTA CCT CTA
                                  F   E   G   F   R   P   S   P   S   L   P   E   P   T   E   L   P   L 1306      1315      1324      1333      1342      1351
                                 CCT CCA CTC CTG CCA CCG CCG CCC TCG ACC ACC GCC CCT CTC CCC ATC CGT
                                  P   P   L   L   P   P   P   P   S   T   T   A   P   L   P   I   R 1360      1369      1378      1387      1396      1405
                                 CCC CCC TCA GGG ACC AAG AAG TCC AAG AGG GGG CGT GGG CGT CCA GGG CGC TAG
                                  P   P   S   G   T   K   K   S   K   R   G   R   G   R   P   G   R   *

1414      1423      1432      1441      1450      1459
                                 GAA GCC GGG TGG GGG TGA GGG TAG CCC TTG AGC CCT GTC CCT GCG GCT GTG AGA 1468      1477      1486      1495      1504      1513
                                 GCA GCA GGA CCC TGG GCC AGT TCC AGA GAC CTG GGG GTG TGT CTG GGG GTG GGG 1522      1531      1540      1549      1558      1567
                                 TGT GAG TGC GTA TGA AAG TGT GTG TCT GCT GGG GCA GCT GGG CCC CTG AAT CAT
```

FIGURE 2D

```
      1576      1585      1594      1603      1612      1621
GGG CAC GGA GGG CCG CCC GCC ACA CCC CGC GCT CAA CTG CTC CCG TGG AAG ATT
      1630      1639
AAA GGG CTG AAT CAT GAA AAA AAA AAA AA 3'
```

FIGURE 2E

```
  1 M P A S Q P I D X P G A K X R G K X N K R G R A T D S F S G  HSTK-2
  1 M P S Q P I D I P D A K K R K K R C R A T D S F S G          GI1929061

31 R F E X V Y X L Q E X X L G E G A H A R V Q T C I N L I T S  HSTK-2
 31 R F E D V Y Q L Q E D V L G E G A H A R V Q T C V N L I T N  GI1929061

61 Q E Y X V X I T X E F X G H I R S R V F R E V E M L Y Q C Q  HSTK-2
 61 Q E Y A V K I H E K Q L G H I R S R V F R E V E M L Y Q C Q  GI1929061

91 G H R N V L E L I E F F E E D R F Y L V F E E K M R G G S I  HSTK-2
 91 G H R N V L E L I E F F E E D R F Y L V F E E K M R G G S I  GI1929061

121 L S H I H K R R H F N E L E A S V V V Q D V A S A L D F L H  HSTK-2
121 L S H I H R R H F N E L E A S V V V Q D V A S A L D F L H    GI1929061

151 N K G I A H R D L K P E N I L C E H P N Q V S P V K I C D F  HSTK-2
151 N K G I A H R D L K P E N I L C E H P N Q V S P V K I C D F  GI1929061

181 D L G S G I K L N G D C S P I S T P E L L T P C G S A E Y M  HSTK-2
181 D L G S G I K L N G D C S P I S T P E L L T P C G S A E Y M  GI1929061

211 A P E V V E A F S E E A S I Y D K R C D L W S L G V I L Y I  HSTK-2
211 A P E V V E A F S E E A S I Y D K R C D L W S L G V I L Y I  GI1929061

241 L L S G Y P P F V G R - - - - W Q R L R L G P L M Y D M      HSTK-2
241 L L S G Y P P F V G H C G S D C G W D R G E A C P A C Q N M  GI1929061
```

FIGURE 3A

```
266  LTGSPPFTAENRKKTMDKIIRGKLALP---    HSTK-2
271  L-------------FESIQEGKYEFFPDKD    GI1929061

293  -PYLTPDARDLVKKFLKRNPSQRIGGPGD    HSTK-2
287  WSHISFAAKDLISKLLVRDAKQRLS---    GI1929061

322  AADVQRHPFFRHMNWDDLLAWRVDPPFRPC    HSTK-2
312  AAQVLQHP---WVQ-------------GC    GI1929061

352  LQSEEDVSQFDTRETRQTPVDSPDDTALSE   HSTK-2
325  ------------APENT-------------   GI1929061

382  SANQAFLGFTYVAPSVLDSIKEGFSFQPKL   HSTK-2
330  ---------LPTPLVLQ----------RN    GI1929061

412  RSPRRLNSSPRVPVSPLKFSPFEGFRPSPS   HSTK-2
340  SCAKDLTS--------FAA-EAIAMNRQ     GI1929061

442  LPEPTELPLPPLLPPPPSTTAPLPIRPPS    HSTK-2
359  LAQCEE-DAGQDQPVVIRATSRCLQLSPPS   GI1929061

472  GTKKS-KRGRGRPGRRKPGGGEGSP        HSTK-2
388  QSKLAQRRQRRASLSATPVVLVGDRA       GI1929061
```

FIGURE 3B

```
  1   - - - - - - - - - - - - - - - - - - - - - - - - M P S R - - - -  HSTK-3
  1   M R R R R R D G F Y P A P D F R D R E A E D M A G V F D I         GI 1562

5   - - - - - - - - - - - - - - - - - - - - - - - - - - - - - -      HSTK-3
 31   D L D Q P E D A G S E D E L E E G G Q L N E S M D H G G V G       GI 1562

5   - - - - - - - - - - - - - - - - - - - - - - - - - - - - - -      HSTK-3
 61   P Y E L G M E H C E K F E I S E T S V N R G P E K I R P E C       GI 1562

5   - - - - - - - - - - - L V A N S T S S - - - - - - - - - - -      HSTK-3
 91   F E L L R V L G K G G Y G K V F Q V R K V T G A N T G K I F       GI 1562

13   - - A M K V L K K A M I V R N A K D T A H T K A E R N I L E E V   HSTK-3
121   A M K V L S A S V V A S S W                                       GI 1562

24   K H P F I V D L I Y A F Q T G G K L Y L I L E Y L S G G E L       HSTK-3
151                                                                    GI 1562

24   F M Q L E R E G I F M E D T A C F Y L A E I S M A L G H L H       HSTK-3
181   - - - - - - - - - E D T A C F Y L A E I T L A L G H L H           GI 1562

43   S Q G I I Y R D L K P E N I M L S S Q G H I K L T D F G L C       HSTK-3
211   Q K G I I Y R D L K P E N I M L N H Q G H V K L T D F G L C       GI 1562

73   K E S I H E G A V T H T F C G T I E Y M A P E I L V R S G H       HSTK-3
241   K E S I H D G T V T H T F C G T I E Y M A P E I L M R S G H       GI 1562
```

FIGURE 4A

FIGURE 4B

```
103 N R A V D W W S L G A L M Y D M L T G S P P F T A E N R K K   HSTK-3
271 N R A V D W W S L G A L M Y D M L T G A P P F T G E N R K K   GI 1562

133 T M D K I I R G K L A L P P Y L T P D A R D L V K K F L K R   HSTK-3
301 T I D K I L K C K L N L P P Y L T Q E A R D L L K K L L K R   GI 1562

163 N P S Q R I G G G P G D A A D V Q R H P F F R H M N W D D L   HSTK-3
331 N A A S R L G A G P G D A G E V Q A H P F F R H I N W E E L   GI 1562

193 L A W R V D P P P F F R P C L Q S E E D V S Q F D T R F T R Q T   HSTK-3
361 L A R K V E P P F K P L L Q S E E D V S Q F D S K F T R Q T   GI 1562

223 P V D S P D D T A L S E S A N Q A F L G F T Y V A P S V L D   HSTK-3
391 P V D S P D D S T L S E S A N Q V F L G F T Y V A P S V L E   GI 1562

253 S I K E G F S F Q P K L R S P R R L N S S P R V P V S P L K   HSTK-3
421 S V K E F S F E P K I R S P R R F I G S P R T P V S P V K   GI 1562

283 F S P F E G F R - - - - P S P S L P E P T E L P L P P -   HSTK-3
451 F S P - G D F W G R G A A S T A N P Q T P V E Y P M E T S   GI 1562

306 - - - - L L P P P P P S T T A P L P I R P P S G T K K S K R   HSTK-3
480 G I E Q M D V T T S G E A S A P L P I R Q P N S G P Y K K Q   GI 1562

332 G - - - R G R P G R   HSTK-3
510 A F P M I S K R P E H L R M N L   GI 1562
```

SERINE/THREONINE PROTEIN KINASES

This application is a continuation-in-part of U.S. patent application Ser. No. 08/749,902, filed Nov. 15, 1996 now U.S. Pat. No. 5,985,635.

FIELD OF THE INVENTION

This invention relates to nucleic acid and amino acid sequences of serine/threonine protein kinases and to the use of these sequences in the diagnosis, treatment, and prevention of cancer, inflammatory diseases, and disorders that affect growth and development.

BACKGROUND OF THE INVENTION

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases.

Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contain specific residues and motifs or patterns of amino acids that are characteristic of that subdomain and are highly conserved. (Hardie, G. and Hanks, S. (1995) *The Protein Kinase Facts Books I*, Academic Press, San Diego, Calif., pp. 7–20).

The second messenger dependent protein kinases primarily mediate the effects of second messengers such as cyclic AMP (cAMP) cyclic GMP, inositol triphosphate, phosphatidylinositol, 3,4,5-triphosphate, cyclic ADP ribose, arachidonic acid and diacylglycerol. The cyclic-AMP dependent protein kinases (PKA) are important members of the STK family. Cyclic-AMP is an intracellular mediator of hormone action in all procaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease. (Isselbacher, K. J. et al. (1994) *Harrison's Principles of Internal Medicine*, McGraw-Hill, New York, N.Y., pp. 416–431).

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) Nature 365:781–783). MAP kinase signaling pathways are present in mammalian cells as well as in yeast. The extracellular stimuli which activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1). An important member of the MAP kinases is the cytoplasmic p70 ribosomal S6 kinase which is essential for the initiation of protein synthesis in all cell types following mitogenic stimulation (Hershey, J. W. B. (1989) J. Biol. Chem. 264: 20823–26). Altered MAP kinase expression can therefore be implicated in a variety of disease conditions including cancer, inflammation, immune disorders, and disorders affecting growth and development.

The discovery of new serine/threonine protein kinases and the polynucleotides encoding them satisfies a need in the art by providing new compositions which are useful in the diagnosis, treatment, and prevention of cancer, inflammatory diseases, and disorders that affect growth and development.

SUMMARY OF THE INVENTION

The invention features substantially purified polypeptides, serine/threonine protein kinases, referred to collectively as "HSTK" and individually as "HSTK-2" and "HSTK-3." In one aspect, the invention provides a substantially purified polypeptide comprising an amino acid sequence selected from the group consisting of SEQ ID NO:1, SEQ ID NO:2, and fragments thereof.

The invention further provides a substantially purified variant having at least 90% amino acid identity to the amino acid sequences of SEQ ID NO:1, SEQ ID NO:2, and fragments thereof. The invention also provides an isolated and purified polynucleotide encoding the polypeptide comprising an amino acid sequence selected from the group consisting of SEQ ID NO:1, SEQ ID NO:2, and fragments thereof. The invention also includes an isolated and purified polynucleotide variant having at least 70% polynucleotide sequence identity to the polynucleotide encoding the polypeptide comprising an amino acid sequence selected from the group consisting of SEQ ID NO:1, SEQ ID NO:2, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, and fragments thereof, as well as an isolated and purified polynucleotide having a sequence which is complementary to the polynucleotide encoding the polypeptide comprising the amino acid sequence selected from the group consisting of SEQ ID NO:1, SEQ ID NO:2, and fragments thereof.

The invention also provides an isolated and purified polynucleotide comprising a polynucleotide sequence selected from the group consisting of SEQ ID NO:3, SEQ ID NO:4, and fragments thereof. The invention further provides an isolated and purified polynucleotide variant having at least 70% polynucleotide sequence identity to the polynucleotide sequence comprising a polynucleotide sequence selected from the group consisting of SEQ ID NO:3, SEQ ID NO:4, and fragments thereof, as well as an isolated and purified polynucleotide having a sequence which is complementary to the polynucleotide comprising a polynucleotide sequence selected from the group consisting of SEQ ID NO:3, SEQ ID NO:4, and fragments thereof.

The invention further provides an expression vector containing at least a fragment of the polynucleotide encoding the polypeptide comprising an amino acid sequence selected from the group consisting of SEQ ID NO:1, SEQ ID NO:2, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, and fragments thereof in conjunction with a suitable pharmaceutical carrier.

The invention further includes a purified antibody which binds to a polypeptide comprising the amino acid sequence selected from the group consisting of SEQ ID NO:1, SEQ ID NO:2, and fragments thereof, as well as a purified agonist and a purified antagonist to the polypeptide.

The invention also provides a method for treating or preventing a cancer, the method comprising administering to a subject in need of such treatment an effective amount of an antagonist of the polypeptide having an amino acid sequence selected from the group consisting of SEQ ID NO:1, SEQ ID NO:2, and fragments thereof.

The invention also provides a method for treating or preventing an inflammatory disorder, the method comprising administering to a subject in need of such treatment an effective amount of an antagonist of the polypeptide having an amino acid sequence selected from the group consisting of SEQ ID NO:1, SEQ ID NO:2, and fragments thereof.

The invention also provides a method for treating or preventing a disorder affecting growth and development, the method comprising administering to a subject in need of such treatment an effective amount of an antagonist of the polypeptide having an amino acid sequence selected from the group consisting of SEQ ID NO:1, SEQ ID NO:2, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

BRIEF DESCRIPTION OF THE FIGURES AND TABLE

FIGS. 1A, 1B, 1C, 1D, and 1E show the amino acid sequence (SEQ ID NO:1) and nucleic acid sequence (SEQ ID NO:3) of HSTK-2.

FIGS. 2A, 2B, 2C, 2D, and 2E show the amino acid sequence (SEQ ID NO:2) and nucleic acid sequence (SEQ ID NO:4) of HSTK-3. The alignments were produced using MACDNASIS PRO software (Hitachi Software Engineering Co. Ltd., Yokohama, Japan).

FIGS. 3A and 3B show the amino acid sequence alignments between HSTK-2 (Incyte clone number 1309709; SEQ ID NO:1) and MAP kinase interacting kinase (GI 1929061; SEQ ID NO:5).

FIGS. 4A and 4B show the amino acid sequence alignments between HSTK-3 (Incyte clone number 2180242; SEQ ID NO:2) and G3 serine/threonine kinase (GI 1562; SEQ ID NO:6). The alignments were produced using the multisequence alignment program of LASERGENE software (DNASTAR Inc, Madison Wis.).

Table 1 summarizes the programs, algorithms, databases, and qualifying scores used to analyze HSTK.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"HSTK" refers to the amino acid sequences of substantially purified HSTK obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to HSTK, increases or prolongs the duration of the effect of HSTK. Agonists may include proteins, nucleic acids, carbohydrates, or any other molecules which bind to and modulate the effect of HSTK.

An "allelic variant" is an alternative form of the gene encoding HSTK. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HSTK include those sequences with deletions, insertions, or substitutions of different nucleotides, resulting in a polynucleotide the same as HSTK or a polypeptide with at least one functional characteristic of HSTK. Included within this definition are polymorphisms which may or may not be readily detectable using a particular oligonucleotide probe of the polynucleotide encoding HSTK, and improper or unexpected hybridization to allelic variants, with a locus other than the normal chromosomal locus for the polynucleotide sequence encoding HSTK. The encoded protein may also be "altered," and may contain deletions, insertions, or substitutions of amino acid residues which produce a silent change and result in a functionally equivalent HSTK. Deliberate amino acid substitutions may be made on the basis of similarity in polarity, charge, solubility, hydrophobicity, hydrophilicity, and/or the amphipathic nature of the residues, as long as the biological or immunological activity of HSTK is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of HSTK which are preferably at least 5 to about 15 amino acids in length, most preferably at least 14 amino acids, and which retain some biological activity or immunological activity of HSTK. Where "amino acid sequence" is recited to refer to an amino acid sequence of a naturally occurring proten molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to HSTK, decreases the amount or the duration of the effect of the biological or immunological activity of HSTK. Antagonists may include proteins, nucleic acids, carbohydrates, antibodies, or any other molecules which decrease the effect of HSTK.

The term "antibody" refers to intact molecules as well as to fragments thereof, such as Fab, F(ab')$_2$, and Fv fragments, which are capable of binding the epitopic determinant. Antibodies that bind HSTK polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic HSTK, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" bonds to the complementary sequence "3' T-C-A 540 ." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding HSTK or fragments of HSTK may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (PE Biosystem, Foster City Calif.) in the 5' and/or the 3' direction, and resequenced, or which has been assembled from the overlapping sequences of more than one Incyte Clone using a computer program for fragment assembly, such as the GELVIEW Fragment Assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding HSTK, by northern analysis is indicative of the presence of nucleic acids encoding HSTK in a sample, and thereby correlates with expression of the transcript from the polynucleotide encoding HSTK.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR) which creates alignments between two or more sequences according to methods selected by the user, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid bonds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of HSTK. For example, modulation may cause an increase or a decrease in protein activity, binding characteristics, or any other biological, functional, or immunological properties of HSTK.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding HSTK, or fragments thereof, or HSTK itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HSTK polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to HSTK. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of new human serine/threonine protein kinases (HSTK), the polynucleotides encoding HSTK, and the use of these compositions for the diagnosis, treatment, or prevention of cancer, inflammatory diseases, and disorders that affect growth and development.

Nucleic acids encoding the HSTK-2 of the present invention were first identified in Incyte Clone 1309709 from the fetal small intestine cDNA library (COLNFET02) using a computer search, e.g., BLAST, for amino acid sequence alignments. A consensus sequence, SEQ ID NO:3, was derived from the following overlapping and/or extended nucleic acid sequences: Incyte Clones 1309709 (COLNFET02), 1281853 (LUNGFET03), 1377014 (LUNGNOT10), 1574640 and 1577736 (LNODNOT03), and 1629855 (COLNPOT01).

In one embodiment, the invention encompasses a polypeptide comprising the amino acid sequence of SEQ ID NO:1, as shown in FIGS. 1A, 1B, 1C, 1D, and 1E. HSTK-2 is 495 amino acids in length and has a potential cAMP- and cGMP-dependent protein kinase phosphorylation site at residue T280. In addition, HSTK-2 has twelve potential casein kinase II phosphorylation sites at residues T59, S144, S196, S223, S354, S359, T369, S373, S396, S400, S431, and S441, as well kinase phosphorylation site at residue Y87 and seven potential protein kinase C phosphorylation sites at residues S29, S312, S400, S413, S420, T473, and S476. HSTK-2 contains a serine/threonine specific protein kinase signature sequence from residues I154 through C166. As shown in FIGS. 3A and 3B, HSTK-2 has chemical and structural similarity with mouse MAP kinase interacting kinase (SEQ ID NO:5; GI 1929061). In particular, HSTK-2 and MAP kinase interacting kinase share 61% identity. A fragment of SEQ ID NO:3 from about nucleotide 1531 to about nucleotide 1591 is useful as a hybridization probe. Northern analysis shows the expression of this sequence in various libraries, at least 60% of which are from proliferative or fetal tissue and at least 40% of which are from tissue associated with the immune response.

Nucleic acids encoding the HSTK-3 of the present invention were first identified in Incyte Clone 2180242 from the ileum tissue cDNA library (SININOT01) using a computer search, e.g., BLAST, for amino acid sequence alignments. A consensus sequence, SEQ ID NO:4, was derived from the following overlapping and/or extended nucleic acid sequences: Incyte Clone 2180242 (SININOT01), 1290913 (BRAINOT11), 683687X48, 683687X24, and 684126X21 (UTRSNOT902), and the shotgun sequence SAFC01675.

In another embodiment, the invention encompasses a polypeptide comprising the amino acid sequence of SEQ ID NO:2, as shown in FIGS. 2A, 2B, 2C, 2D, and 2E. HSTK-3 is 338 amino acids in length, and has a potential N-glycosylation site at residue N8. In addition, HSTK-3 has a potential cAMP- and cGMP-dependent protein kinase phosphorylation site at residue T133, eleven potential casein kinase II phosphorylation sites at residues S21, S22, S75, S207, S212, T222, S226, S249, S253, S284, and S294, and six potential protein kinase C phosphorylation sites at residues S15, S253, S266, S273, T326, and S329. HSTK-3 contains a serine/threonine specific protein kinase signature sequence from residues I46 through L58. As illustrated by FIGS. 4A and 4B, HSTK-3 and rabbit G3 serine/threonine kinase (SEQ ID NO:6; GI 1562). In particular, HSTK-3 and rabbit G3 serine/threonine kinase share 64% identity. A fragment of SEQ ID NO:4 from about nucleotide 1342 to about nucleotide 1402 is useful as a hybridization probe. Northern analysis shows the expression of this sequence in various libraries, at least 60% of which are cancerous or proliferative, and at least 35% of which involve immune response. Of particular note is the expression of HSTK-3 in reproductive tissue tumors.

The invention also encompasses HSTK variants. A preferred HSTK variant is one which has at least about 80%, more preferably at least about 90%, and most preferably at least about 95% amino acid sequence identity to the HSTK amino acid sequence, and which contains at least one functional or structural characteristic of HSTK.

It will be appreciated by those skilled in the art that as a result of the degeneracy of the genetic code, a multitude of polynucleotide sequences encoding HSTK, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HSTK, and all such variations are to be considered as being specifically disclosed.

Although nucleotide sequences which encode HSTK and its variants are preferably capable of hybridizing to the nucleotide sequence of the naturally occurring HSTK under appropriately selected conditions of stringency, it may be advantageous to produce nucleotide sequences encoding HSTK or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSTK and its derivatives without altering the encoded amino acid sequences include the production of RNA transcripts having more desirable properties, such as a greater half-life, than transcripts produced from the naturally occurring sequence.

The invention also encompasses production of DNA sequences which encode HSTK and HSTK derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HSTK or any fragment thereof.

Also encompassed by the invention are polynucleotide sequences that are capable of hybridizing to the claimed polynucleotide sequences, and, in particular, to those shown in SEQ ID NO:3, SEQ ID NO:4, and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/mnl denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE, Taq polymerase, thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 (Hamilton, Reno Nev.), DNA ENGINE thermal cycler (PTC200; MJ Research, Watertown Mass.) and the ABI CATALYST 800 (PE Biosystems). Sequencing is then carried out using either ABI 373 or 377 DNA sequencing systems (PE Biosystems) or the MEGABACE 1000 DNA sequencing system (Molecular Dynamics, Sunnyvale Calif.). The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding HSTK may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, software, PE Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HSTK may be cloned in recombinant DNA molecules that direct expression of HSTK, or fragments or functional equivalents thereof, in appropriate host cells. Due to the inherent degeneracy of the genetic code, other DNA sequences which encode substantially the same or a functionally equivalent amino acid sequence may be produced and used to express HSTK.

The nucleotide sequences of the present invention can be engineered using methods generally known in the art in order to alter HSTK-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HSTK may be synthesized, in whole or in part, using chemical methods well known in the art. (See, e.g., Caruthers, M. H. et al. (1980) Nucl. Acids Symp. Ser. 215–223, and Horn, T. et al. (1980) Nucl. Acids Symp. Ser. 225–232.) Alternatively, HSTK itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431 A Peptide synthesizer (PE Biosystems). Additionally, the amino acid sequence of HSTK, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, W H Freeman, New York N.Y.)

In order to express a biologically active HSTK, the nucleotide sequences encoding HSTK or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HSTK. Such elements may vary in their strength and specificity. Specific initiation signals may also be used to achieve more efficient translation of sequences encoding HSTK. Such signals include the ATG initiation codon and adjacent sequences, e.g. the Kozak sequence. In cases where sequences encoding HSTK and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding HSTK and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding HSTK. These include, but are not limited to, microorganisms such as bacteria transformed with recombinant bacteriophage, plasmid, or cosmid DNA expression vectors; yeast transformned with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HSTK. For example, routine cloning, subcloning, and propagation of polynucleotide sequences encoding HSTK can be achieved using a multifunctional *E. coli* vector such as PBLUESCRIPT phagemid (Stratagene, La Jolla Calif.) or pSPORT1 plasmid (Life Technologies). Ligation of sequences encoding HSTK into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of HSTK are needed, e.g. for the production of antibodies, vectors which direct high level expression of HSTK may be used. For example, vectors containing the strong, inducible T5 or T7 bacteriophage promoter may be used.

Yeast expression systems may be used for production of HSTK. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516–54; and Scorer, C. A. et al. (1994) Bio/Technology 12:181–184.)

Plant systems may also be used for expression of HSTK. Transcription of sequences encoding HSTK may be driven viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding HSTK may be ligated into an adenovirus transcription/translation complex consisting of the late promoter and tripartite leader sequence. Insertion in a non-essential E1 or E3 region of the viral genome may be used to obtain infective virus which expresses HSTK in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345–355.)

For long term production of recombinant proteins in mammalian systems, stable expression of HSTK in cell lines is preferred. For example, sequences encoding HSTK can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding HSTK is inserted within a marker gene sequence, transformed cells containing sequences encoding HSTK can be identified by the absence of marker gene function. Alternatively, a marker gene can be placed in tandem with a sequence encoding HSTK under the control of a single promoter. Expression of the marker gene in response to induction or selection usually indicates expression of the tandem gene as well.

In general, host cells that contain the nucleic acid sequence encoding HSTK and that express HSTK may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HSTK using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HSTK is preferred, but a competitive binding assay may be employed. These and other assays are well known in the art. (See, e.g., Hampton, R. et al. (1990) Serological Methods, a Laboratory Manual, APS Press, St Paul Minn., Sect. IV; Coligan, J. E. et al. (1997) Current Protocols in Immunology, Greene Pub. Associates and Wiley-Interscience, New York N.Y.; and Pound, J. D. (1998) Immunochemical Protocols, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding HSTK include oligolabeling, nick translation, end-labeling, or PCR amplification using a labeled nucleotide. Alternatively, the sequences encoding HSTK, or any fragments thereof, may be cloned into a vector for the production of an MRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech and Promega (Madison Wis.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HSTK may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HSTK may be designed to contain signal sequences which direct secretion of HSTK through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda Md.) and may be chosen to ensure the correct modification and processing of the foreign protein.

In another embodiment of the invention, natural, modified, or recombinant nucleic acid sequences encoding HSTK may be ligated to a heterologous sequence resulting in translation of a fusion protein in any of the aforementioned host systems. For example, a chimeric HSTK protein containing a heterologous moiety that can be recognized by a commercially available antibody may facilitate the screening of peptide libraries for inhibitors of HSTK activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-mnyc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HSTK encoding sequence and the heterologous protein sequence, so that HSTK may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled HSTK may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HSTK may be produced not only by recombinant production, but also by direct peptide synthesis using solid-phase techniques. (See, e.g., Creighton, supra, pp. 55–60.) Protein synthesis may be performed by manual techniques or by automation. Automated synthesis may be achieved, for example, using the ABI 431A Peptide synthesizer (PE Biosystems). Various fragments of HSTK may be synthesized separately and then combined to produce the full length molecule.

Therapeutics

Chemical and structural similarity, e.g., in the context of sequences and motifs, exists between regions of HSTK and MAP kinase interacting kinase from mouse (GI 1929061). In addition, HSTK-2 is expressed in proliferative or fetal tissue, and in tissues associated with the immune response. Chemical and structural similarity exists between HSTK-3 and G3 serine/threonine kinase from rabbit (GI 1562). In addition, HSTK-3 is expressed in libraries associated with cancerous or proliferative tissues and in libraries associated with immune response tissue. Therefore, HSTK appears to be upregulated in cancer, inflammatory diseases, and disorders that affect growth and development.

Therefore, in one embodiment, an antagonist of HSTK may be administered to a subject to treat or prevent a disorder associated with increased expression or activity of HSTK. Examples of such disorders include, but are not limited to, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory diseases such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and disorders that affects growth and development such as renal tubular acidosis, anemia, Cushing's syndrome, achondroplastic dwarfism, Duchenne and Becker muscular dystrophy, epilepsy, gonadal dysgenesis, WAGR syndrome, Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss. In one aspect, an antibody which specifically binds HSTK may be used directly as an antagonist or indirectly as a targeting or delivery mechanism for bringing a pharmaceutical agent to cells or tissue which express HSTK.

In an additional embodiment, a vector expressing the complement of the polynucleotide encoding HSTK may be administered to a subject to treat or prevent those disorders described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HSTK may be produced using methods which are generally known in the art. In particular, purified HSTK may be used to produce antibodies or to screen libraries of pharmaceutical agents to identify those which specifically bind HSTK. Antibodies to HSTK may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HSTK or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HSTK have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HSTK amino acids may be fused with those of another protein, such as KLH, and antibodies to the chimeric molecule may be produced.

Monoclonal antibodies to HSTK may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:3142; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HSTK-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; Winter, G. et al. (1991) Nature 349:293–299.)

Antibody fragments which contain specific binding sites for HSTK may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSTK and its specific antibody. A two-site, monoclonal-based immunoassay utilizing monoclonal antibodies reactive to two non-interfering HSTK epitopes is preferred, but a competitive binding assay may also be employed (Pound, supra).

Various methods such as Scatchard analysis in conjunction with radioimmunoassay techniques may be used to assess the affinity of antibodies for HSTK. Affinity is expressed as an association constant, $K_a$, which is defined as the molar concentration of HSTK-antibody complex divided by the molar concentrations of free antigen and free antibody under equilibrium conditions. The $K_a$ determined for a preparation of polyclonal antibodies, which are heterogeneous in their affinities for multiple HSTK epitopes, represents the average affinity, or avidity, of the antibodies for HSTK. The $K_a$ determined for a preparation of monoclonal antibodies, which are monospecific for a particular HSTK epitope, represents a true measure of affinity. High-affinity antibody preparations with $K_a$ ranging from about $10^9$ to $10^{12}$ L/mole are preferred for use in immunoassays in which the HSTK-antibody complex must withstand rigorous manipulations. Low-affinity antibody preparations with $K_a$ ranging from about $10^6$ to $10^7$ L/mole are preferred for use in immunopurification and similar procedures which ultimately require dissociation of HSTK, preferably in active form, from the antibody (Catty, D. (1988) *Antibodies, Volume I: A Practical Approach*, IRL Press, Washington, D.C.; Liddell, J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of HSTK-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding HSTK, or any fragment or complement thereof, may be used for therapeutic purposes. In one aspect, the complement of the polynucleotide encoding HSTK may be used in situations in which it would be desirable to block the transcription of the mRNA. In particular, cells may be transformed with sequences complementary to polynucleotides encoding HSTK. Thus, complementary molecules or fragments may be used to modulate HSTK activity, or to achieve regulation of gene function. Such technology is now well known in the art, and sense or antisense oligonucleotides or larger fragments can be designed from various locations along the coding or control regions of sequences encoding HSTK.

Expression vectors derived from retroviruses, adenoviruses, or herpes or vaccinia viruses, or from various bacterial plasrnids, may be used for delivery of nucleotide sequences to the targeted organ, tissue, or cell population. Methods which are well known to those skilled in the art can be used to construct vectors to express nucleic acid sequences complementary to the polynucleotides encoding HSTK. (See, e.g., Sambrook, supra; Ausubel, 1995, supra.)

Genes encoding HSTK can be turned off by transforming a cell or tissue with expression vectors which express high levels of a polynucleotide, or fragment thereof, encoding HSTK. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HSTK. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HSTK.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSTK. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HSTK, antibodies to HSTK, and mimetics, agonists, antagonists, or inhibitors of HSTK. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HSTK, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HSTK or fragments thereof, antibodies of HSTK, and agonists, antagonists or inhibitors of HSTK, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio between therapeutic and toxic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSTK may be used for the diagnosis of cancer, inflammatory diseases, and disorders that affect growth and development characterized by expression of HSTK, or in assays to monitor patients being treated with HSTK or agonists, antagonists, or inhibitors of HSTK. Antibodies useful for diagnostic purposes may be prepared in the same manner as described above for therapeutics. Diagnostic assays for HSTK include methods which utilize the antibody and a label to detect HSTK in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HSTK, including ELISAs, RIAs, and FACS, are known in the art and provide a basis for diagnosing altered or abnormal levels of HSTK expression. Normal or standard values for HSTK expression are established by combining body fluids or cell extracts taken from normal mammalian subjects, preferably human, with antibody to HSTK under conditions suitable for complex formation. The amount of standard complex formation may be quantitated by various methods, preferably by photometric means. Quantities of HSTK expressed in subject, control, and disease samples from biopsied tissues are compared with the standard values. Deviation between standard and subject values establishes the parameters for diagnosing disease.

In another embodiment of the invention, the polynucleotides encoding HSTK may be used for diagnostic purposes.

The polynucleotides which may be used include oligonucleotide sequences, complementary RNA and DNA molecules, and PNAs. The polynucleotides may be used to detect and quantitate gene expression in biopsied tissues in which expression of HSTK may be correlated with disease. The diagnostic assay may be used to determine absence, presence, and excess expression of HSTK, and to monitor regulation of HSTK levels during therapeutic intervention.

In one aspect, hybridization with PCR probes which are capable of detecting polynucleotide sequences, including genomic sequences, encoding HSTK or closely related molecules may be used to identify nucleic acid sequences which encode HSTK. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HSTK, allelic variants, or related sequences.

Probes may also be used for the detection of related sequences, and should preferably have at least 50% sequence identity to any of the HSTK encoding sequences. The hybridization probes of the subject invention may be DNA or RNA and may be derived from SEQ ID NO:3, SEQ ID NO:4, or fragments thereof or from genomic sequences including promoters, enhancers, and introns of the HSTK gene.

Means for producing specific hybridization probes for DNAs encoding HSTK include the cloning of polynucleotide sequences encoding HSTK or HSTK derivatives into vectors for the production of MRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}p$ or $^{35}S$, or by enzymatic labels, such as alkaline phosphatase coupled to the probe via avidinfbiotin coupling systems, and the like.

Polynucleotide sequences encoding HSTK may be used for the diagnosis of a disorder associated with expression of HSTK. Examples of such a disorder include, but are not limited to, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, inflammatory diseases such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma, and disorders that affect growth and development such as tubular acidosis, anemia, Cushing's syndrome, achondroplastic dwarfism, Duchenne and Becker muscular dystrophy, epilepsy, gonadal dysgenesis, WAGR syndrome, Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss. The polynucleotide sequences encoding HSTK may be used in Southern or Northern analysis, dot blot, or other membrane-based technologies; in PCR technologies; in dipstick, pin, and ELISA-like assays; and in microarrays utilizing fluids or tissues from patients to detect altered HSTK expression. Such qualitative or quantitative methods are well known in the art.

In a particular aspect, the nucleotide sequences encoding HSTK may be useful in assays that detect the presence of associated disorders, particularly those mentioned above. The nucleotide sequences encoding HSTK may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HSTK in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HSTK, a normal or standard profile for expression is established. This may be accomplished by combining body fluids or cell extracts taken from normal subjects, either animal or human, with a sequence, or a fragment thereof, encoding HSTK, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSTK may involve the use of PCR. These oligomers may be chemically synthesized, generated enzymatically, or produced in vitro. Oligomers will preferably contain a fragment of a polynucleotide encoding HSTK, or a fragment of a polynucleotide complementary to the polynucleotide encoding HSTK, and will be employed under optimized conditions for identification of a specific gene or condition. Oligomers may also be employed under less stringent conditions for detection or quantitation of closely related DNA or RNA sequences.

Methods which may also be used to quantitate the expression of HSTK include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in an ELISA-like format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HSTK may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correlation between the location of the gene encoding HSTK on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HSTK, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HSTK and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with HSTK, or fragments thereof, and washed. Bound HSTK is then detected by methods well known in the art. Purified HSTK can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSTK specifically compete with a test compound for binding HSTK. In this manner, antibodies can be used to detect the presence of any peptide which shares one or more antigenic determinants with HSTK.

In additional embodiments, the nucleotide sequences which encode HSTK may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

The COLNFET02 cDNA library was constructed using RNA isolated from colon tissue obtained from a 20-week-old fetus. The pregnant mother was treated with erythromycin for seven days in the first trimester for bronchitis. The SININOT01 library was constructed using RNA isolated from ileum tissue obtained from the small intestine of a 4-year-old Caucasian female, who died from a closed head injury. For both libraries, the frozen tissue was homogenized and lysed using a POLYTRON homogenizer (PT-3000)

(Brinkmann Instruments, Westbury N.J.) in guanidinium isothiocyanate solution. The lysate was centrifuged over a 5.7 M CsCl cushion using a SW28 rotor in a L8-70M Ultracentrifuge (Beckman Coulter, Fullerton Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNase at 37° C. The RNA extraction was repeated with acid phenol pH 4.7 and precipitated with sodium acetate and ethanol as before. The mRNA was then isolated using the OLIGOTEX kit (QIAGEN, Inc. Chatsworth Calif.) and used to construct the cDNA libraries. The mRNA was handled according to the recommended protocols in the SUPERSCRIPT plasmid system (Life Technologies). The resulting cDNAs were fractionated on a SEPHAROSE CL4B column (Amersham Pharmacia Biotech), and those cDNAs exceeding 400 bp were ligated into pINCY (Incyte Pharmaceuticals, Palo Alto Calif.). The plasmid pINCY I was subsequently transformed into DH5α competent cells (Life Technologies).

II. Isolation of cDNA Clones

Plasmid DNA was released from the cells and purified using the REAL PREP 96 plasmid kit (QIAGEN, Inc.). The recommended protocol was employed except for the following changes: 1) the bacteria were cultured in 1 ml of sterile Terrific Broth (Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

III. Sequencing and Analysis

The cDNAs were prepared for sequencing using the ABI CATALYST 800 (Perkin-Elmer) or the HYDRA microdispenser (Robbins Scientific) or MICROLAB 2200 (Hamilton) systems in combination with the DNA ENGINE thermal cyclers (MJ Research). The cDNAs were sequenced using the ABI PRISM 373 or 377 sequencing systems (PE Biosystems) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE Terminator cycle sequencing ready reaction kit (PE Biosystems). In yet another alternative, cDNAs were sequenced using solutions and dyes from Amersham Pharmacia Biotech. Reading frames for the ESTs were determined using standard methods (reviewed in Ausubel, 1997, upra, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 1 shows the tools, programs, and algorithms used, provides a brief description thereof, and presents the references which are incorporated by reference herein and where applicable, the scores, probability values, and other parameters used to evaluate the strength of a match between two sequences (the higher the probability the greater the homology). Sequences were analyzed using MACDNASIS PRO software (Hitachi Software Engineering) and LASERGENE software (DNASTAR).

The polynucleotide sequences were validated by removing vector, linker, and polyA sequences and by masking ambiguous bases, using algorithms and programs based on BLAST, dynamic programming, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, PFAM, and Prosite.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported a percentage distribution of libraries in which the transcript encoding HSTK occurred. Analysis involved the categorization of cDNA libraries by organ/tissue and disease. The organ/tissue categories included cardiovascular, dermatologic, developmental, endocrine, gastrointestinal, hematopoietic/ immune, musculoskeletal, nervous, reproductive, and urologic. The disease categories included cancer, inflammation/ trauma, fetal, neurological, and pooled. For each category, the number of libraries expressing the sequence of interest was counted and divided by the total number of libraries across all categories. Percentage values of tissue-specific and disease expression are reported in the description of the invention.

V. Extension of HSTK Encoding Polynucleotides

The full length nucleic acid sequences of SEQ ID NO:3 and SEQ ID NO:4 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the DNA ENGINE thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1× TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly, Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethylsulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (PE Biosystems).

In like manner, the nucleotide sequence of SEQ ID NO:2 is used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:3 or SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [$^{32}$P]-adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN).

The DNA from each digest is fractionated on a 0.7% agarose gel and transferred to nylon membranes (NYTRAN PLUS, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT-AR film (Eastman Kodak, Rochester N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HSTK-encoding sequences, or any parts thereof, are used to detect, decrease, or inhibit expression of naturally occurring HSTK. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of HSTK. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSTK-encoding transcript.

IX. Expression of HSTK

Expression and purification of HSTK is achieved using bacterial or virus-based expression systems. For expression of HSTK in bacteria, cDNA is subcdoned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HSTK upon induction with isopropyl beta-D-thiogalactopyranoside (IPTG). Expression of HSTK in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HSTK by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. U.S.A. 91:3224–3227; Sandig, V. et al. (1996) Hum. Gene Ther. 7:1937–1945.)

In most expression systems, HSTK is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from HSTK at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified HSTK obtained by these methods can be used directly in the following activity assay.

X. Demonstration of HSTK Activity

HSTK activity may be measured by phosphorylation of a protein substrate using γ-labeled $^{32}$P-ATP and quantitation of the incorporated radioactivity using a gamma radioisotope counter. For example, to measure activity of MAP kinase interacting kinase, purified inactivated MAP kinase protein is used as substrate (see, e.g., Flotow, H. and Thomas, G. (1992) J. Biol. Chem. 267: 3074–78). HSTK is incubated with the protein substrate, $^{32}$P-ATP, and a kinase buffer. The $^{32}$P incorporated into the substrate is then separated from free $^{32}$P-ATP by electrophoresis and the incorporated $^{32}$P is counted. A determination of the specific amino acid residues phosphorylated is made by phosphoamino acid analysis of the hydrolyzed protein as described by Boyle, W. J. et al (1991) Methods in Enzymol. 201: 110–148.

XI. Functional Assays

HSTK function is assessed by expressing the sequences encoding HSTK at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3. 1 (Invitrogen, Carlsbad Calif.), both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate cellular properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of HSTK on gene expression can be assessed using highly purified populations of cells transfected with sequences encoding HSTK and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HSTK and other genes of interest can be analyzed by northern analysis or microarray techniques.

XII. Production of HSTK Specific Antibodies

HSTK substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the HSTK amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431A Peptide synthesizer (PE systems) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HSTK Using Specific Antibodies

Naturally occurring or recombinant HSTK is substantially purified by immunoaffinity chromatography using antibodies specific for HSTK. An immunoaffinity column is constructed by covalently coupling anti-HSTK antibody to an activated chromatographic resin, such as CNBr-activated SEPHAROSE (Amersham Pharmacia Biotech). After the coupling, the resin is blocked and washed according to the manufacturer's instructions.

Media containing HSTK are passed over the immunoaffinity column, and the column is washed under conditions that allow the preferential absorbance of HSTK (e.g., high ionic strength buffers in the presence of detergent). The column is eluted under conditions that disrupt antibody/HSTK binding (e.g., a buffer of pH 2 to pH 3, or a high concentration of a chaotrope, such as urea or thiocyanate ion), and HSTK is collected.

XIV. Identification of Molecules Which Interact with HSTK

HSTK, or biologically active fragments thereof, are labeled with $^{125}$I Bolton-Hunter reagent. (See, e.g., Bolton et al. (1973) Biochem. J. 133:529–539.) Candidate molecules previously arrayed in the wells of a multi-well plate are incubated with the labeled HSTK, washed, and any wells with labeled HSTK complex are assayed. Data obtained using different concentrations of HSTK are used to calculate values for the number, affinity, and association of HSTK with the candidate molecules. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Program | Description | Reference | Parameter Threshold |
| --- | --- | --- | --- |
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403–410; Altschul, S. F. et al. (1997) Nucleic Acids Res. 25: 3389–3402. | ESTs: Probability value = 1.08E-8 or less Full Length sequences: Probability value = 1.0E-10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85: 2444–2448; Pearson, W. R. (1990) Methods Enzymol. 183: 63–98; and Smith, T. F. and M. S. Waterman (1981) Adv. Appl. Math. 2: 482–489. | ESTs: fasta E value = 1.06E-6 Assembled ESTs: fasta Identity = 95% or greater and Match length = 200 bases or greater; fastx E value = 1.08E-8 or less Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19: 6565–72, 1991. J. G. Henikoff and S. Henikoff (1996) Methods Enzymol. 266: 88–105; and Attwood, T. K. et al. (1997) J. Chem. Inf. Comput. Sci. 37: 417–424. | Score = 1000 or greater; Ratio of Score/Strength = 0.75 or larger; and Probability value = 1.0E-3 or less |
| PFAM | A Hidden Markov Models-based application useful for protein family search. | Krogh, A. et al. (1994) J. Mol. Biol., 235: 1501–1531; Sonnhammer, E. L. L. et al. (1988) Nucleic Acids Res. 26: 320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4: 61–66; Gribskov, et al. (1989) Methods Enzymol. 183: 146–159; Bairoch, A. et al. (1997) Nucleic Acids Res. 25: 217–221. | Score = 4.0 or greater |
| Phred | A base-calling algorithm that examines automated sequencer traces with high sensitivity and probability. | Ewing, B. et al. (1998) Genome Res. 8: 175–185; Ewing, B. and P. Green (1998) Genome Res. 8: 186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482–489; Smith, T. F. and M. S. Waterman (1981) J. Mol. Biol. 147: 195–197; and Green, P., University of Washington, Seattle, WA. | Score = 120 or greater; Match length = 56 or greater |
| Consed | A graphical tool for viewing and editing | Gordon, D. et al. (1998) Genome Res. | |

TABLE 1-continued

| Program | Description | Reference | Parameter Threshold |
|---|---|---|---|
| | Phrap assemblies | 8: 195–202. | |
| SPScan | A weight matrix analysis program that scans protein sequences for the presence of secretory signal peptides. | Nielson, H. et al. (1977) Protein Engineering 10: 1–6; Claverie, J. M. and S. Audic (1997) CABIOS 12: 431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. A substantially purified polypeptide comprising an amino acid sequence selected from the group consisting of SEQ ID NO:1 and SEQ ID NO:2.

2. A pharmaceutical composition comprising the polypeptide of claim 1 in conjunction with a suitable pharmaceutical carrier.

3. A method for using a polypeptide to screen a library of molecules or compounds to identify at least one molecule or compound which specifically binds the polypeptide, the method comprising:
   a) combining the polypeptide of claim 1 with the library of molecules or compounds under conditions to allow specific binding; and
   b) detecting specific binding, thereby identifying a molecule or compound which specifically binds the polypeptide.

4. The method of claim 3 wherein the library of molecules or compounds is selected from the group consisting of DNA molecules, peptides, agonists, antagonists, antibodies, immunoglobulins and pharmaceutical agents.

5. A method of using a polypeptide to purify a molecule or compound which specifically binds the polypeptide from a sample, the method comprising:
   a) combining the polypeptide of claim 1 with a sample under conditions to allow specific binding;
   b) recovering the bound polypeptide; and
   c) separating the polypeptide from the molecule or compound, thereby obtaining purified molecule or compound from the sample.

* * * * *

SEQUENCE LISTING

```
<160> NUMBER OF SEQ ID NOS: 6

<210> SEQ ID NO 1
<211> LENGTH: 495
<212> TYPE: PRT
<213> ORGANISM: Homo sapiens
<220> FEATURE:
<221> NAME/KEY: unsure
<221> NAME/KEY: unsure
<222> LOCATION: 9, 14, 18, 34, 37, 41, 42, 64, 66, 69, 72
<222> LOCATION:
<223> OTHER INFORMATION: unknown, or other
<220> FEATURE: -
<223> OTHER INFORMATION: >1309709

<400> SEQUENCE: 1

Met Pro Ala Ser Gln Pro Ile Asp Xaa Pro Gly Ala Lys Xaa Arg
  1               5                  10                  15

Gly Lys Xaa Asn Lys Arg Gly Arg Ala Thr Asp Ser Phe Ser Gly
                 20                  25                  30

Arg Phe Glu Xaa Val Tyr Xaa Leu Gln Glu Xaa Xaa Leu Gly Glu
                 35                  40                  45

Gly Ala His Ala Arg Val Gln Thr Cys Ile Asn Leu Ile Thr Ser
                 50                  55                  60

Gln Glu Tyr Xaa Val Xaa Ile Ile Xaa Phe Phe Xaa Gly His Ile
                 65                  70                  75

Arg Ser Arg Val Phe Arg Glu Val Glu Met Leu Tyr Gln Cys Gln
                 80                  85                  90

Gly His Arg Asn Val Leu Glu Leu Ile Glu Phe Phe Glu Glu Glu
                 95                 100                 105

Asp Arg Phe Tyr Leu Val Phe Glu Lys Met Arg Gly Gly Ser Ile
                110                 115                 120

Leu Ser His Ile His Lys Arg Arg His Phe Asn Glu Leu Glu Ala
                125                 130                 135

Ser Val Val Gln Asp Val Ala Ser Ala Leu Asp Phe Leu His His
                140                 145                 150

Asn Lys Gly Ile Ala His Arg Asp Leu Lys Pro Glu Asn Ile Leu
                155                 160                 165

Cys Glu His Pro Asn Gln Val Ser Pro Val Lys Ile Cys Asp Phe
                170                 175                 180

Asp Leu Gly Ser Gly Ile Lys Leu Asn Gly Asp Cys Ser Pro Ile
                185                 190                 195

Ser Thr Pro Glu Leu Leu Thr Pro Cys Gly Ser Ala Glu Tyr Met
                200                 205                 210

Ala Pro Glu Val Val Glu Ala Phe Ser Glu Glu Ala Ser Ile Tyr
```

-continued

```
                215                 220                 225

Asp Lys Arg Cys Asp Leu Trp Ser Leu Gly Val Ile Leu Tyr Ile
            230                 235                 240

Leu Leu Ser Gly Tyr Pro Pro Phe Val Gly Arg Trp Trp Gln Arg
            245                 250                 255

Leu Arg Leu Gly Pro Leu Met Tyr Asp Met Leu Thr Gly Ser Pro
            260                 265                 270

Pro Phe Thr Ala Glu Asn Arg Lys Thr Met Asp Lys Ile Ile
            275                 280                 285

Arg Gly Lys Leu Ala Leu Pro Pro Tyr Leu Thr Pro Asp Ala Arg
            290                 295                 300

Asp Leu Val Lys Lys Phe Leu Lys Arg Asn Pro Ser Gln Arg Ile
            305                 310                 315

Gly Gly Gly Pro Gly Asp Ala Ala Asp Val Gln Arg His Pro Phe
            320                 325                 330

Phe Arg His Met Asn Trp Asp Leu Leu Ala Trp Arg Val Asp
            335                 340                 345

Pro Pro Phe Arg Pro Cys Leu Gln Ser Glu Glu Asp Val Ser Gln
            350                 355                 360

Phe Asp Thr Arg Phe Thr Arg Gln Thr Pro Val Asp Ser Pro Asp
            365                 370                 375

Asp Thr Ala Leu Ser Glu Ser Ala Asn Gln Ala Phe Leu Gly Phe
            380                 385                 390

Thr Tyr Val Ala Pro Ser Val Leu Asp Ser Ile Lys Glu Gly Phe
            395                 400                 405

Ser Phe Gln Pro Lys Leu Arg Ser Pro Arg Arg Leu Asn Ser Ser
            410                 415                 420

Pro Arg Val Pro Val Ser Pro Leu Lys Phe Ser Pro Phe Glu Gly
            425                 430                 435

Phe Arg Pro Ser Pro Ser Leu Pro Glu Pro Thr Glu Leu Pro Leu
            440                 445                 450

Pro Pro Leu Leu Pro Pro Pro Pro Ser Thr Thr Ala Pro Leu
            455                 460                 465

Pro Ile Arg Pro Pro Ser Gly Thr Lys Lys Ser Lys Arg Gly Arg
            470                 475                 480

Gly Arg Pro Gly Arg Arg Lys Pro Gly Gly Gly Glu Gly Ser Pro
            485                 490                 495

<210> SEQ ID NO 2
<211> LENGTH: 338
<212> TYPE: PRT
<213> ORGANISM: Homo sapiens
<220> FEATURE: -
<223> OTHER INFORMATION: >2180242

<400> SEQUENCE: 2

Met Pro Ser Arg Leu Val Ala Asn Ser Thr Ser Ser Leu Ser Ala
  1               5                  10                  15

Ser Val Val Ala Ser Ser Ser Trp Glu Asp Thr Ala Cys Phe Tyr
            20                  25                  30

Leu Ala Glu Ile Thr Leu Ala Leu Gly His Leu His Ser Gln Gly
            35                  40                  45

Ile Ile Tyr Arg Asp Leu Lys Pro Glu Asn Ile Met Leu Ser Ser
            50                  55                  60

Gln Gly His Ile Lys Leu Thr Asp Phe Gly Leu Cys Lys Glu Ser
```

```
                         65                  70                  75
Ile His Glu Gly Ala Val Thr His Thr Phe Cys Gly Thr Ile Glu
                 80                  85                  90
Tyr Met Ala Pro Glu Ile Leu Val Arg Ser Gly His Asn Arg Ala
                 95                 100                 105
Val Asp Trp Trp Ser Leu Gly Ala Leu Met Tyr Asp Met Leu Thr
                110                 115                 120
Gly Ser Pro Pro Phe Thr Ala Glu Asn Arg Lys Lys Thr Met Asp
                125                 130                 135
Lys Ile Ile Arg Gly Lys Leu Ala Leu Pro Pro Tyr Leu Thr Pro
                140                 145                 150
Asp Ala Arg Asp Leu Val Lys Lys Phe Leu Lys Arg Asn Pro Ser
                155                 160                 165
Gln Arg Ile Gly Gly Gly Pro Gly Asp Ala Ala Asp Val Gln Arg
                170                 175                 180
His Pro Phe Phe Arg His Met Asn Trp Asp Asp Leu Leu Ala Trp
                185                 190                 195
Arg Val Asp Pro Pro Phe Arg Pro Cys Leu Gln Ser Glu Glu Asp
                200                 205                 210
Val Ser Gln Phe Asp Thr Arg Phe Thr Arg Gln Thr Pro Val Asp
                215                 220                 225
Ser Pro Asp Asp Thr Ala Leu Ser Glu Ser Ala Asn Gln Ala Phe
                230                 235                 240
Leu Gly Phe Thr Tyr Val Ala Pro Ser Val Leu Asp Ser Ile Lys
                245                 250                 255
Glu Gly Phe Ser Phe Gln Pro Lys Leu Arg Ser Pro Arg Arg Leu
                260                 265                 270
Asn Ser Ser Pro Arg Val Pro Val Ser Pro Leu Lys Phe Ser Pro
                275                 280                 285
Phe Glu Gly Phe Arg Pro Ser Pro Ser Leu Pro Glu Pro Thr Glu
                290                 295                 300
Leu Pro Leu Pro Pro Leu Leu Pro Pro Pro Pro Ser Thr Thr
                305                 310                 315
Ala Pro Leu Pro Ile Arg Pro Pro Ser Gly Thr Lys Lys Ser Lys
                320                 325                 330
Arg Gly Arg Gly Arg Pro Gly Arg
                335

<210> SEQ ID NO 3
<211> LENGTH: 1607
<212> TYPE: DNA
<213> ORGANISM: Homo sapiens
<220> FEATURE:
<221> NAME/KEY: unsure
<221> NAME/KEY: unsure
<222> LOCATION: 6, 13, 16, 28, 32, 42, 73, 78, 79, 125, 142, 154, 200,
      211,
<222> LOCATION: 221, 224, 290, 298, 306, 314, 973
<223> OTHER INFORMATION: a or g or c or t, unknown, or other
<220> FEATURE: -
<223> OTHER INFORMATION: >1309709

<400> SEQUENCE: 3
gtatcnctgc canggnggcc cccacccnaa ancaggggg tngggccgg ccggccaggg    60 ccatgtcctg agnccccnng gcgtgcctcc tggaacagat atgcccgcca gccagccat  120 tgacntcccg ggcgccaaga anaggggcaa gaanaataag cgcggccggg ccaccgacag 180
```

-continued

```
cttctcgggc aggttttgaan acgtctacca nctgcaggaa natntgctgg gggagggcgc      240
tcatgcccga gtgcagacct gcattaacct gatcaccagc caggagtacn ccgtcaanat      300 cattgnttttt tttncaggcc acattcggag cagggttttc agggaggtgg agatgctgta     360
ccagtgccag ggacacagga acgtcctaga gctgattgag ttcttcgagg aggaggaccg      420
cttctacctg gtgtttgaga agatgcgggg aggctccatc ctgagccaca tccacaagcg      480
ccggcacttc aacgagctgg aggccagcgt ggtggtgcag gacgtggcca gcgccttgga      540
ctttctgcat aacaaaggca tcgcccacag ggacctaaag ccggaaaaca tcctctgtga      600
gcaccccaac caggtctccc ccgtgaagat ctgtgacttc gacctgggca gcggcatcaa      660
actcaacggg gactgctccc ctatctccac cccggagctg ctcactccgt gcggctcggc      720
ggagtacatg gccccggagg tagtggaggc cttcagcgag gaggctagca tctacgacaa      780
gcgctgcgac ctgtggagcc tgggcgtcat cttgtatatc ctactcagcg gctacccgcc      840
cttcgtgggc cgctggtggc agcgactgcg gctgggaccg ctgatgtacg acatgctcac      900
tggatcgccg ccctttaccg cagagaaccg gaagaaaacc atggataaga tcatcagggg      960
caagctggca ctncccccct acctcacccc agatgcccgg gaccttgtca aaagtttct     1020 gaaacggaat cccagccagc ggattggggg tggcccaggg gatgctgctg atgtgcagag     1080
acatcccttt ttccggcaca tgaattggga cgaccttctg gcctggcgtg tggacccccc     1140
tttcaggccc tgtctgcagt cagaggagga cgtgagccag tttgataccc gcttcacacg     1200
gcagacgccg gtggacagtc ctgatgacac agccctcagc gagagtgcca accaggcctt     1260
cctgggcttc acatacgtgg cgccgtctgt cctggacagc atcaaggagg gcttctcctt     1320
ccagcccaag ctgcgctcac ccaggcgcct caacagtagc cccgggtcc ccgtcagccc      1380 cctcaagttc tccccttttg aggggtttcg gcccagcccc agcctgccgg agcccacgga     1440
gctacctcta cctccactcc tgccaccgcc ccgccctcg accaccgccc ctctccccat      1500
ccgtcccccc tcagggacca agaagtccaa gaggggccgt gggcgtccag ggcgtaggaa     1560
gccgggtggg ggtgagggta gcccttgagc cctgtccctg cggctgt                   1607
```

<210> SEQ ID NO 4
<211> LENGTH: 1647
<212> TYPE: DNA
<213> ORGANISM: Homo sapiens
<220> FEATURE:
<221> NAME/KEY: unsure
<222> LOCATION: 31, 32
<223> OTHER INFORMATION: a or g or c or t, unknown, or other
<220> FEATURE: -
<223> OTHER INFORMATION: >2180242

<400> SEQUENCE: 4

```
cgacgggccc gcggcggcgc gccatggcgc nngtgtttga tttggatttg gagacggagg       60
aaggcagcga gggcgagggc gagccagagc tcagccccgc ggcctgtggg acactatgaa      120
gaggtggagc tgactgagac cagcgtgaac gttggcccag agcgcatcgg gccccactgc      180
tttgagctgc tgcgtgtgct gggcaagggg ggctatggca aggtgttcca ggtgcgaaag      240
gtgcaaggca ccaacttggg caaaatatat gccatgaaag tcctaaggaa ggccaaaatt      300
gtgcgcaatg ccaaggacac agcacacaca cgggctgagc ggaacattct agagtcagtg      360
aagcacccct ttattgtgga actggcctat gccttccaga ctggtggcaa actctacctc      420
gtccttgagt gcctcagtgg tggcgagctc ttcctggaa gatacggcct gcttctacct      480
ggctgagatc acgctggccc tgggccatct ccactcccag gcatcatct accgggacct      540
```

-continued

```
caagcccgag aacatcatgc tcagcagcca gggccacatc aaactgaccg actttggact    600
ctgcaaggag tcaatccatg agggcgccgt cactcacacc ttctgcggca ccattgagta    660
catggcccct gagattctgg tgcgcagtgg ccacaaccgg gctgtggact ggtggagcct    720
gggggccctg atgtacgaca tgctcactgg atcgccgccc tttaccgcag agaaccggaa    780
gaaaaccatg gataagatca tcaggggcaa gctggcactg cccccctacc tcaccccaga    840
tgcccgggac cttgtcaaaa agtttctgaa acggaatccc agccagcgga ttgggggtgg    900
cccaggggat gctgctgatg tgcagagaca tcccttttc cggcacatga attgggacga    960
ccttctggcc tggcgtgtgg acccccttt caggccctgt ctgcagtcag aggaggacgt   1020
gagccagttt gataccccgct tcacacggca gacgccggtg gacagtcctg atgacacagc   1080
cctcagcgag agtgccaacc aggccttcct gggcttcaca tacgtggcgc cgtctgtcct   1140
ggacagcatc aaggagggct ctccttcca gcccaagctg cgctcaccca ggcgcctcaa   1200
cagtagcccc cgggtccccg tcagcccct caagttctcc ccttttgagg ggtttcggcc   1260
cagccccagc ctgccggagc ccacggagct acctctacct ccactcctgc caccgccgcc   1320
gccctcgacc accgcccctc tccccatccg tcccccctca gggaccaaga agtccaagag   1380
ggggcgtggg cgtccagggc gctaggaagc cgggtggggg tgagggtagc ccttgagccc   1440
tgtccctgcg gctgtgagag cagcaggacc ctgggccagt tccagagacc tgggggtgtg   1500
tctgggggtg gggtgtgagt gcgtatgaaa gtgtgtgtct gctggggcag ctgtgcccct   1560
gaatcatggg cacggagggc cgcccgccac accccgcgct caactgctcc cgtggaagat   1620
taaagggctg aatcatgaaa aaaaaaa                                       1647
```

<210> SEQ ID NO 5
<211> LENGTH: 412
<212> TYPE: PRT
<213> ORGANISM: Mus musculus
<220> FEATURE: -
<223> OTHER INFORMATION: >GI1929061

<400> SEQUENCE: 5

```
Met Pro Ser Ser Gln Pro Ile Asp Ile Pro Asp Ala Lys Lys Arg
  1               5                  10                  15

Gly Arg Lys Lys Lys Arg Cys Arg Ala Thr Asp Ser Phe Ser Gly
                 20                  25                  30

Arg Phe Glu Asp Val Tyr Gln Leu Gln Glu Asp Val Leu Gly Glu
                 35                  40                  45

Gly Ala His Ala Arg Val Gln Thr Cys Val Asn Leu Ile Thr Asn
                 50                  55                  60

Gln Glu Tyr Ala Val Lys Ile Ile Glu Lys Gln Leu Gly His Ile
                 65                  70                  75

Arg Ser Arg Val Phe Arg Glu Val Glu Met Leu Tyr Gln Cys Gln
                 80                  85                  90

Gly His Arg Asn Val Leu Glu Leu Ile Glu Phe Phe Glu Glu Glu
                 95                 100                 105

Asp Arg Phe Tyr Leu Val Phe Glu Lys Met Arg Gly Gly Ser Ile
                110                 115                 120

Leu Ser His Ile His Arg Arg Arg His Phe Asn Glu Leu Glu Ala
                125                 130                 135

Ser Val Val Val Gln Asp Val Ala Ser Ala Leu Asp Phe Leu His
                140                 145                 150
```

-continued

```
Asn Lys Gly Ile Ala His Arg Asp Leu Lys Pro Glu Asn Ile Leu
            155                 160                 165

Cys Glu His Pro Asn Gln Val Ser Pro Val Lys Ile Cys Asp Phe
            170                 175                 180

Asp Leu Gly Ser Gly Ile Lys Leu Asn Gly Asp Cys Ser Pro Ile
            185                 190                 195

Ser Thr Pro Glu Leu Leu Thr Pro Cys Gly Ser Ala Glu Tyr Met
            200                 205                 210

Ala Pro Glu Val Val Glu Ala Phe Ser Glu Glu Ala Ser Ile Tyr
            215                 220                 225

Asp Lys Arg Cys Asp Leu Trp Ser Leu Gly Val Ile Leu Tyr Ile
            230                 235                 240

Leu Leu Ser Gly Tyr Pro Pro Phe Val Gly His Cys Gly Ser Asp
            245                 250                 255

Cys Gly Trp Asp Arg Gly Glu Ala Cys Pro Ala Cys Gln Asn Met
            260                 265                 270

Leu Phe Glu Ser Ile Gln Glu Gly Lys Tyr Glu Phe Pro Asp Lys
            275                 280                 285

Asp Trp Ser His Ile Ser Phe Ala Ala Lys Asp Leu Ile Ser Lys
            290                 295                 300

Leu Leu Val Arg Asp Ala Lys Gln Arg Leu Ser Ala Ala Gln Val
            305                 310                 315

Leu Gln His Pro Trp Val Gln Gly Cys Ala Pro Glu Asn Thr Leu
            320                 325                 330

Pro Thr Pro Leu Val Leu Gln Arg Asn Ser Cys Ala Lys Asp Leu
            335                 340                 345

Thr Ser Phe Ala Ala Glu Ala Ile Ala Met Asn Arg Gln Leu Ala
            350                 355                 360

Gln Cys Glu Glu Asp Ala Gly Gln Asp Gln Pro Val Val Ile Arg
            365                 370                 375

Ala Thr Ser Arg Cys Leu Gln Leu Ser Pro Pro Ser Gln Ser Lys
            380                 385                 390

Leu Ala Gln Arg Arg Gln Arg Ala Ser Leu Ser Ala Thr Pro Val
            395                 400                 405

Val Leu Val Gly Asp Arg Ala
            410

<210> SEQ ID NO 6
<211> LENGTH: 525
<212> TYPE: PRT
<213> ORGANISM: Oryctolagus cuniculus
<220> FEATURE: -
<223> OTHER INFORMATION: >GI1562

<400> SEQUENCE: 6

Met Arg Arg Arg Arg Arg Asp Gly Phe Tyr Pro Ala Pro Asp
  1               5                  10                  15

Phe Arg Asp Arg Glu Ala Glu Asp Met Ala Gly Val Phe Asp Ile
             20                  25                  30

Asp Leu Asp Gln Pro Glu Asp Ala Gly Ser Glu Asp Glu Leu Glu
             35                  40                  45

Glu Gly Gly Gln Leu Asn Glu Ser Met Asp His Gly Gly Val Gly
             50                  55                  60

Pro Tyr Glu Leu Gly Met Glu His Cys Glu Lys Phe Glu Ile Ser
             65                  70                  75
```

-continued

```
Glu Thr Ser Val Asn Arg Gly Pro Lys Ile Arg Pro Glu Cys
             80                  85                  90

Phe Glu Leu Leu Arg Val Leu Gly Lys Gly Gly Tyr Gly Lys Val
             95                 100                 105

Phe Gln Val Arg Lys Val Thr Gly Ala Asn Thr Gly Lys Ile Phe
            110                 115                 120

Ala Met Lys Val Leu Lys Lys Ala Met Ile Val Arg Asn Ala Lys
            125                 130                 135

Asp Thr Ala His Thr Lys Ala Glu Arg Asn Ile Leu Glu Glu Val
            140                 145                 150

Lys His Pro Phe Ile Val Asp Leu Ile Tyr Ala Phe Gln Thr Gly
            155                 160                 165

Gly Lys Leu Tyr Leu Ile Leu Glu Tyr Leu Ser Gly Gly Glu Leu
            170                 175                 180

Phe Met Gln Leu Glu Arg Glu Gly Ile Phe Met Glu Asp Thr Ala
            185                 190                 195

Cys Phe Tyr Leu Ala Glu Ile Ser Met Ala Leu Gly His Leu His
            200                 205                 210

Gln Lys Gly Ile Ile Tyr Arg Asp Leu Lys Pro Glu Asn Ile Met
            215                 220                 225

Leu Asn His Gln Gly His Val Lys Leu Thr Asp Phe Gly Leu Cys
            230                 235                 240

Lys Glu Ser Ile His Asp Gly Thr Val Thr His Thr Phe Cys Gly
            245                 250                 255

Thr Ile Glu Tyr Met Ala Pro Glu Ile Leu Met Arg Ser Gly His
            260                 265                 270

Asn Arg Ala Val Asp Trp Trp Ser Leu Gly Ala Leu Met Tyr Asp
            275                 280                 285

Met Leu Thr Gly Ala Pro Pro Phe Thr Gly Glu Asn Arg Lys Lys
            290                 295                 300

Thr Ile Asp Lys Ile Leu Lys Cys Lys Leu Asn Leu Pro Pro Tyr
            305                 310                 315

Leu Thr Gln Glu Ala Arg Asp Leu Leu Lys Lys Leu Leu Lys Arg
            320                 325                 330

Asn Ala Ala Ser Arg Leu Gly Ala Gly Pro Gly Asp Ala Gly Glu
            335                 340                 345

Val Gln Ala His Pro Phe Phe Arg His Ile Asn Trp Glu Glu Leu
            350                 355                 360

Leu Ala Arg Lys Val Glu Pro Pro Phe Lys Pro Leu Leu Gln Ser
            365                 370                 375

Glu Glu Asp Val Ser Gln Phe Asp Ser Lys Phe Thr Arg Gln Thr
            380                 385                 390

Pro Val Asp Ser Pro Asp Asp Ser Thr Leu Ser Glu Ser Ala Asn
            395                 400                 405

Gln Val Phe Leu Gly Phe Thr Tyr Val Ala Pro Ser Val Leu Glu
            410                 415                 420

Ser Val Lys Glu Lys Phe Ser Phe Glu Pro Lys Ile Arg Ser Pro
            425                 430                 435

Arg Arg Phe Ile Gly Ser Pro Arg Thr Pro Val Ser Pro Val Lys
            440                 445                 450

Phe Ser Pro Gly Asp Phe Trp Gly Arg Gly Ala Ser Ala Ser Thr
            455                 460                 465

Ala Asn Pro Gln Thr Pro Val Glu Tyr Pro Met Glu Thr Ser Gly
```

-continued

```
                        470                     475                     480
Ile Glu Gln Met Asp Val Thr Thr Ser Gly Glu Ala Ser Ala Pro
                485                     490                     495
Leu Pro Ile Arg Gln Pro Asn Ser Gly Pro Tyr Lys Lys Gln Ala
                500                     505                     510
Phe Pro Met Ile Ser Lys Arg Pro Glu His Leu Arg Met Asn Leu
                515                     520                     525
```